United States Patent
Chalupper et al.

(10) Patent No.: US 10,798,504 B2
(45) Date of Patent: Oct. 6, 2020

(54) BIMODAL HEARING STIMULATION SYSTEM AND METHOD OF FITTING THE SAME

(71) Applicant: Advanced Bionics AG, Staefa (CH)

(72) Inventors: Josef Chalupper, Paunzhausen (DE); Gunnar Geissler, Hannover (DE)

(73) Assignee: Advanced Bionics AG, Staefa (CH)

( * ) Notice: Subject to any disclaimer, the term of this patent is extended or adjusted under 35 U.S.C. 154(b) by 149 days.

(21) Appl. No.: 16/003,033

(22) Filed: Jun. 7, 2018

(65) Prior Publication Data

US 2018/0288541 A1 Oct. 4, 2018

Related U.S. Application Data

(63) Continuation-in-part of application No. PCT/EP2015/078988, filed on Dec. 8, 2015.

(51) Int. Cl.
*A61N 1/36* (2006.01)
*H04R 25/00* (2006.01)
*A61B 5/12* (2006.01)
*H04R 29/00* (2006.01)

(52) U.S. Cl.
CPC ............ *H04R 25/70* (2013.01); *A61B 5/123* (2013.01); *A61N 1/36038* (2017.08); *A61N 1/36039* (2017.08); *H04R 25/606* (2013.01); *H04R 29/008* (2013.01); *H04R 2225/43* (2013.01); *H04R 2225/67* (2013.01)

(58) Field of Classification Search
CPC .... H04R 25/70; H04R 25/606; H04R 29/008; H04R 2225/43; H04R 2225/67; A61N 1/36036; A61N 1/36039; A61N 1/36038; A61B 5/123
See application file for complete search history.

(56) References Cited

U.S. PATENT DOCUMENTS

| | | | |
|---|---|---|---|
| 2010/0280307 A1* | 11/2010 | Lineaweaver | A61N 1/36036 600/25 |
| 2012/0109006 A1 | 5/2012 | James et al. | |
| 2012/0245655 A1 | 9/2012 | Spitzer et al. | |
| 2013/0218237 A1* | 8/2013 | Svirsky | A61N 1/36032 607/57 |
| 2014/0105408 A1 | 4/2014 | Lievens | |
| 2014/0275730 A1* | 9/2014 | Lievens | A61N 1/36039 600/25 |

(Continued)

OTHER PUBLICATIONS

International Search Report received in PCT Patent Application No. PCT/EP2015/078988, dated Aug. 16, 2016.

*Primary Examiner* — Amanda K Hulbert
*Assistant Examiner* — Natasha Patel
(74) *Attorney, Agent, or Firm* — ALG Intellectual Property, LLC (57) ABSTRACT

A system includes a first device for neural stimulation of a patient's ipsilateral ear and a second hearing stimulation device, wherein the stimulation mode of the second stimulation device is different from that of the first stimulation device. The system further includes a fitting device for adjusting the first stimulation device and the second stimulation device. The fitting device includes a graphical user interface configured to present an acoustic level audiogram representation of aided acoustic and electric behavioral values for the first and second stimulation devices.

23 Claims, 8 Drawing Sheets

(56) References Cited

U.S. PATENT DOCUMENTS

| | | | |
|---|---|---|---|
| 2015/0215710 A1* | 7/2015 | Francart | A61N 1/36036 381/326 |
| 2015/0335890 A1* | 11/2015 | Fredelake | A61N 1/0541 607/57 |
| 2015/0341731 A1 | 11/2015 | Polak | |

* cited by examiner

BIMODAL HEARING STIMULATION SYSTEM AND METHOD OF FITTING THE SAME

RELATED APPLICATIONS

The present application is a continuation-in-part application of PCT International Application No. PCT/EP2015/078988, filed Dec. 8, 2015, the contents of which are hereby incorporated by reference in their entirety.

BACKGROUND INFORMATION

Typically, bimodal hearing stimulation systems combine neural stimulation, e.g. by a cochlear implant and acoustic stimulation. Cochlear implants comprise an electrode array for electrical stimulation of the cochlea at various stimulation sites determined by the position of the respective electrode. Typical systems for bimodal stimulation of the hearing comprise a cochlear implant at the ipsilateral ear and a device for acoustic stimulation of the ipsilateral ear or the contralateral ear. Systems with electric and acoustic stimulation of the same ear are also known as hybrid devices or EAS devices. In systems with contralateral acoustic stimulation the acoustic stimulation device typically is an (electro-acoustic) hearing aid; alternatively, acoustic stimulation can be achieved by a bone conduction hearing aid.

For fitting a bimodal stimulation device a fitting device is connected to the electric stimulation device and the acoustic stimulation device in order to adjust the respective stimulation parameters individually so as to optimize the hearing impression of the patient. In a relatively simple model, the impact of the stimulation parameters may be described by the input/output (I/O) curves of the electric stimulation and the acoustic stimulation. For acoustic stimulation, the I/O curve represents the output level provided by the loudspeaker as the function of the input sound level at the microphone; the acoustic stimulation I/O curves vary as a function of the frequency (or the frequency band) of the audio signal (in a hearing instrument, the input audio signals are divided into various frequency channels for further signal processing). For electrical stimulation, the I/O curves represent the stimulation current for each stimulation channel (e.g. for each stimulation electrode) as a function of the input sound level at the microphone.

A fitting device typically has a graphical user interface which allows the audiologist to see the characteristic audiometric data of the patient, such as the hearing threshold level and the most comfortable level for various stimulation frequencies (such audiogram representation is typically used for fitting of acoustic stimulation devices, such as hearing aids) and allows the audiologist to manually adjust the stimulation parameters, such as the I/O curves of the acoustic stimulation for the patient, thereby individually optimizing the respective aided threshold and most comfortable levels.

For electrical stimulation the fitting device typically uses a representation in the graphical user interface which is different from that of a fitting device for a hearing aid; in particular, the graphical user interface of a fitting device for electrical stimulation typically shows the stimulation currents for each electrode which correspond to the hearing threshold level and/or the most comfortable level.

Further, the workflows for fitting of acoustic stimulation devices and for fitting electric stimulation devices typically are very different, so that usually an audiologist in a clinic where CI devices and bimodal stimulation devices are implanted is not familiar with the fitting of acoustic stimulation devices. Further, for fitting of acoustic stimulation devices air conduction thresholds and an estimate of the vent size for the patient are required.

Thus, the fitting of electroacoustic (i.e. bimodal) hearing systems, both for ipsi- and contralateral stimulation, is counterintuitive, difficult-to-use and inefficient for the audiologist. A consequence for the patient is that the patient often will not receive the optimum individual fitting with bimodal systems.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

The systems and methods described herein relate to a bimodal hearing stimulation system comprising a first device for neural stimulation of the cochlea at one ear, a second device for stimulation of the same ear or the other ear by using a stimulation mode different from that of the first device and a fitting device for individually adjusting the stimulation devices to the patient.

The systems and methods described herein provide for a bimodal stimulation system which enables fitting of both a neural stimulation device and a second stimulation device using a stimulation mode different from that of the neural device in an easy-to-understand and convenient manner.

The systems and methods described herein are beneficial in that, by presenting in the graphical user interface an acoustic level audiogram representation of the aided hearing threshold levels, the aided most comfortable levels and/or the aided uncomfortable levels as a function of the audiometric frequency represented by the respective frequency band of the input audio signal for both stimulation modes, both stimulation devices can be fitted in an easy-to-understand and convenient manner even without knowledge of the technical characteristics of the stimulation devices (e.g. number and center frequencies of the filterbank). In particular, the stimulation levels for both stimulation modes are visualized in a comparable and meaningful manner. Such fitting device allows to expedite the clinical workflow, making fitting of the bimodal stimulation device easier and faster.

Figure 1:
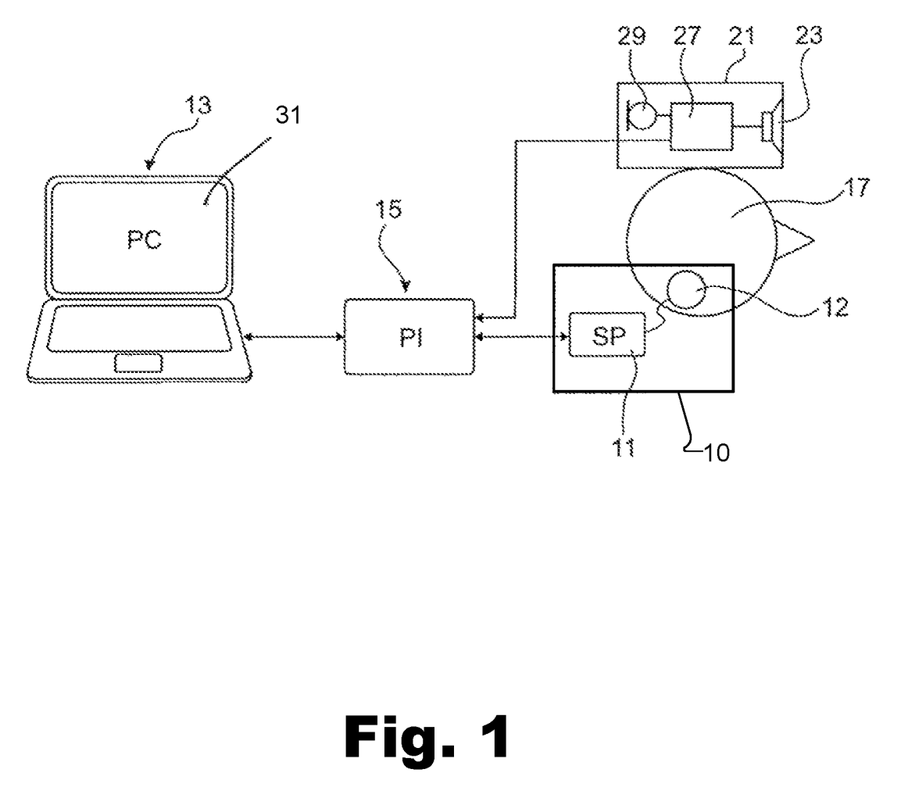
FIG. 1 is a schematic representation of an example of a system according to principles described herein.

FIG. 1 is a schematic representation of an example of a bimodal stimulation system, comprising a fitting/programming unit 13, which may be implemented as a computer, a programming interface 15, a CI device 10 comprising a sound processing subsystem 11 and an implantable stimulation subsystem 12 and being worn by a patient 17 at the ipsilateral ear, and a hearing aid 21 worn at the contralateral ear and comprising a loudspeaker 23 for acoustic stimulation of the contralateral ear. The programming unit 13 communicates with the sound processing subsystem 11 and with the hearing aid 21 via the programming interface 15, which may be implemented as a wired or wireless connection (alternatively, there may be separate programming interfaces for electric and acoustic stimulation).

The programming unit 13 serves to control the sound processing subsystem 11 of the CI device 10 such that probe neural stimulation signals may be applied to the ipsilateral ear of the patient 17 via the stimulation subsystem 12 and to control the hearing aid 21 such that probe acoustic stimulation signals are presented via the loudspeaker 23 to the contralateral ear of the patient 17. Such probe stimulation signals may be presented separately (i.e. subsequently/independently) for acoustic and electric stimulation, or the probe stimulation signals may be presented for acoustic and electric stimulation in a synchronized manner. The perceptual behavioral response of the patient 17 to the such stimulation is recorded by the programming unit 13 via a user interface, which may be part of the programming unit (such as the computer keyboard) or may be provided separately (as schematically indicated at 25 in FIG. 1), in order to be used in the fitting of the CI device 10 and the hearing aid 21, respectively, as will be explained below in detail.

It is to be understood that the programming unit 13 is used with the CI device 10 and the hearing aid 21 only for adjustment/fitting, but not during normal operation of the CI device 10 and the hearing aid 21.

In case that the fitting/programming unit 13 is adapted to generate audio signals/stimulation signals on its own, the programming interface 15 may be replaced by an audio interface for supplying the audio signals generated by the fitting/programming unit 13 to the CI device.

Figure 2:
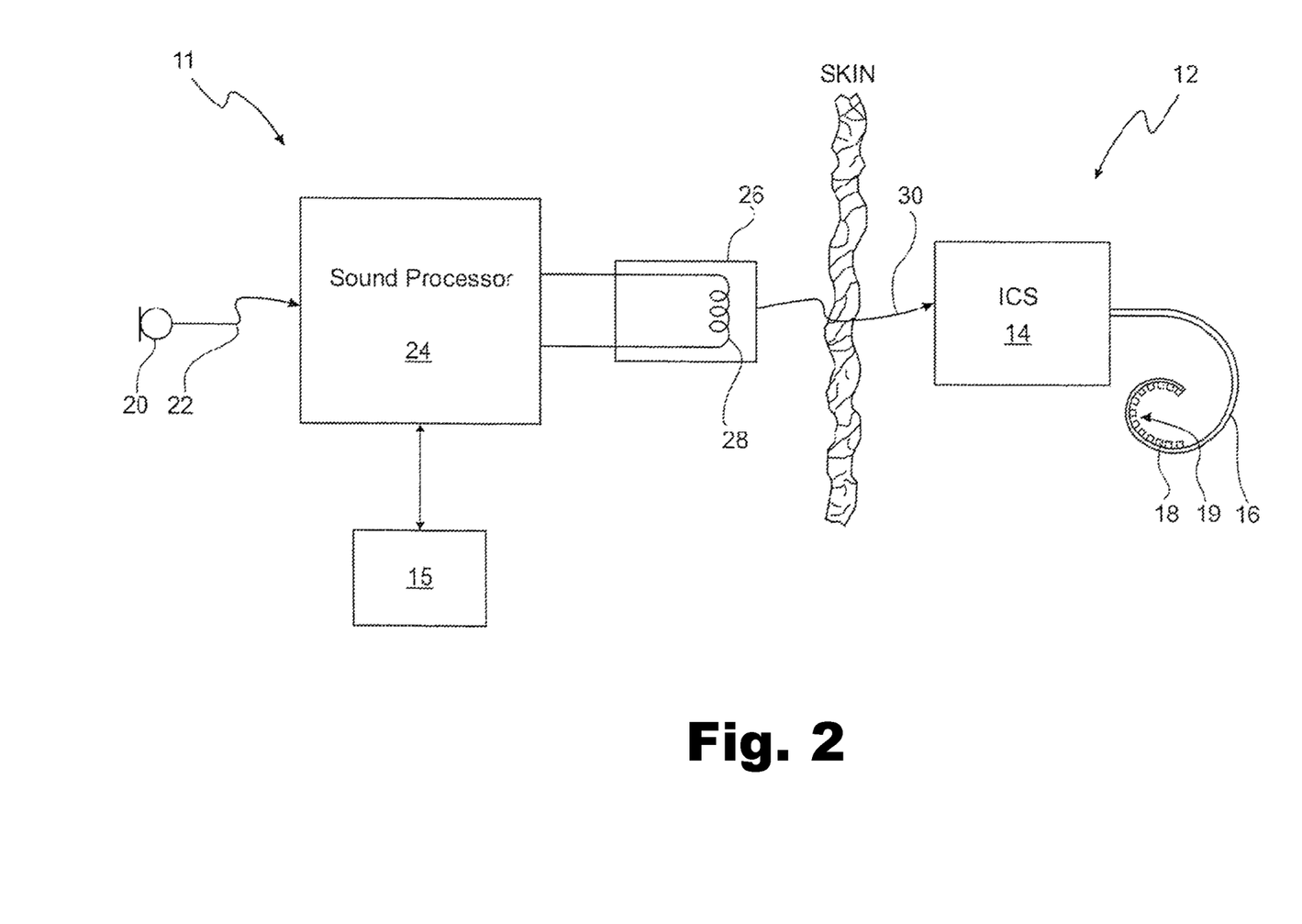
FIG. 2 is a schematic representation of an example of the CI device of FIG. 1 according to principles described herein.

In FIG. 2 an example of the cochlear implant device 10 of the system of FIG. 1 is shown schematically. The sound processing sub-system 11 serves to detect or sense an audio signal and divide the audio signal into a plurality of analysis channels, each containing a frequency domain signal (or simply "signal") representative of a distinct frequency portion of the audio signal. A signal level value is determined for each analysis channel by analyzing the respective frequency domain signal Stimulation parameters are generated based on the frequency domain signal and are transmitted to the stimulation sub-system 12.

Stimulation sub-system 12 serves to generate and apply electrical stimulation (also referred to herein as "stimulation current" and/or "stimulation pulses") to stimulation sites at the auditory nerve within the cochlea of a patient 17 in accordance with the stimulation parameters received from the sound processing sub-system 11. Electrical stimulation is provided to the patient 17 via a CI stimulation assembly 18 comprising a plurality of stimulation channels. The stimulation parameters may control various parameters of the electrical stimulation applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, spectral tilt, ramp-on time, and ramp-off time of the stimulation current that is applied to the stimulation site.

Figure 3:
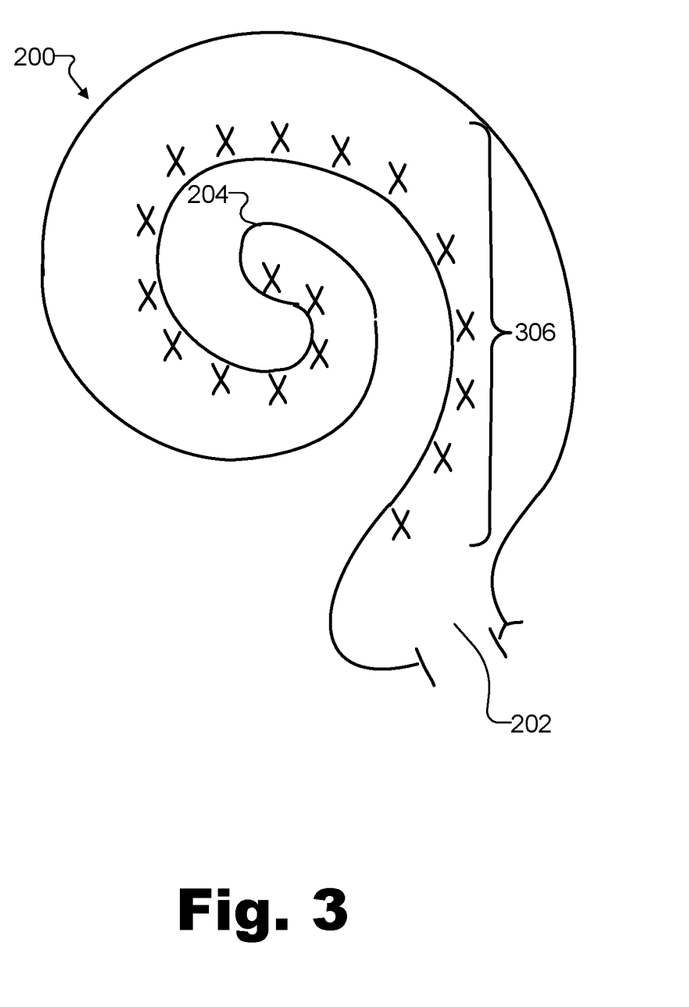
FIG. 3 is a schematic cross section of a human cochlea with marked stimulation sites according to principles described herein.

FIG. 3 illustrates a schematic structure of the human cochlea 200. As shown in FIG. 3, the cochlea 200 is in the shape of a spiral beginning at a base 202 and ending at an apex 204. Within the cochlea 200 resides auditory nerve tissue 206 which is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Stimulation subsystem 12 is configured to apply stimulation to different locations within the cochlea 200 (e.g., different locations along the auditory nerve tissue 206) to provide a sensation of hearing.

Returning to FIG. 2, sound processing subsystem 11 and stimulation subsystem 12 is configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels and threshold current levels (as will be discussed in more detail below), input dynamic range parameters, channel acoustic gain parameters, front and backend dynamic range parameters, current steering parameters, amplitude values, pulse rate values, pulse width values, polarity values, filter characteristics, and/or any other control parameter as may serve a particular application. In particular, the control parameters may include a frequency allocation table (FAT) which determines the respective frequency range allocated to a certain electrode.

In the example shown in FIG. 2, the stimulation sub-system 12 comprises an implantable cochlear stimulator ("ICS") 14, a lead 16 and the stimulation assembly 18 disposed on the lead 16. The stimulation assembly 18 comprises a plurality of "stimulation contacts" 19 for electrical stimulation of the auditory nerve. The lead 16 may be inserted within a duct of the cochlea in such a manner that the stimulation contacts 19 are in communication with one or more stimulation sites within the cochlea, i.e. the stimulation contacts 19 are adjacent to, in the general vicinity of, in close proximity to, directly next to, or directly on the respective stimulation site.

In the example shown in FIG. 2, the sound processing sub-system 11 is designed as being located external to the patient 17; however, in alternative examples, at least one of the components of the sub-system 11 may be implantable.

In the example shown in FIG. 2, the sound processing sub-system 11 comprises a microphone 20 which captures audio signals from ambient sound, a microphone link 22, a sound processor 24 which receives audio signals from the microphone 20 via the link 22, and a headpiece 26 having a coil 28 disposed therein. The sound processor 24 is configured to process the captured audio signals in accordance with a selected sound processing strategy to generate appropriate stimulation parameters for controlling the ICS 14 and may include, or be implemented within, a behind-the-ear (BTE) unit or a portable speech processor ("PSP"). In the example of FIG. 2 the sound processor 24 is configured to transcutaneously transmit data (in particular data representative of one or more stimulation parameters) to the ICS 14 via a wireless transcutaneous communication link 30. The headpiece 26 may be affixed to the patient's head and positioned such that the coil 28 is communicatively coupled to the corresponding coil (not shown) included within the ICS 14 in order to establish the link 30. The link 30 may include a bidirectional communication link and/or one or more dedicated unidirectional communication links. According to an alternative embodiment, the sound processor 24 and the ICS 14 may be directly connected by wires.

Figure 4:
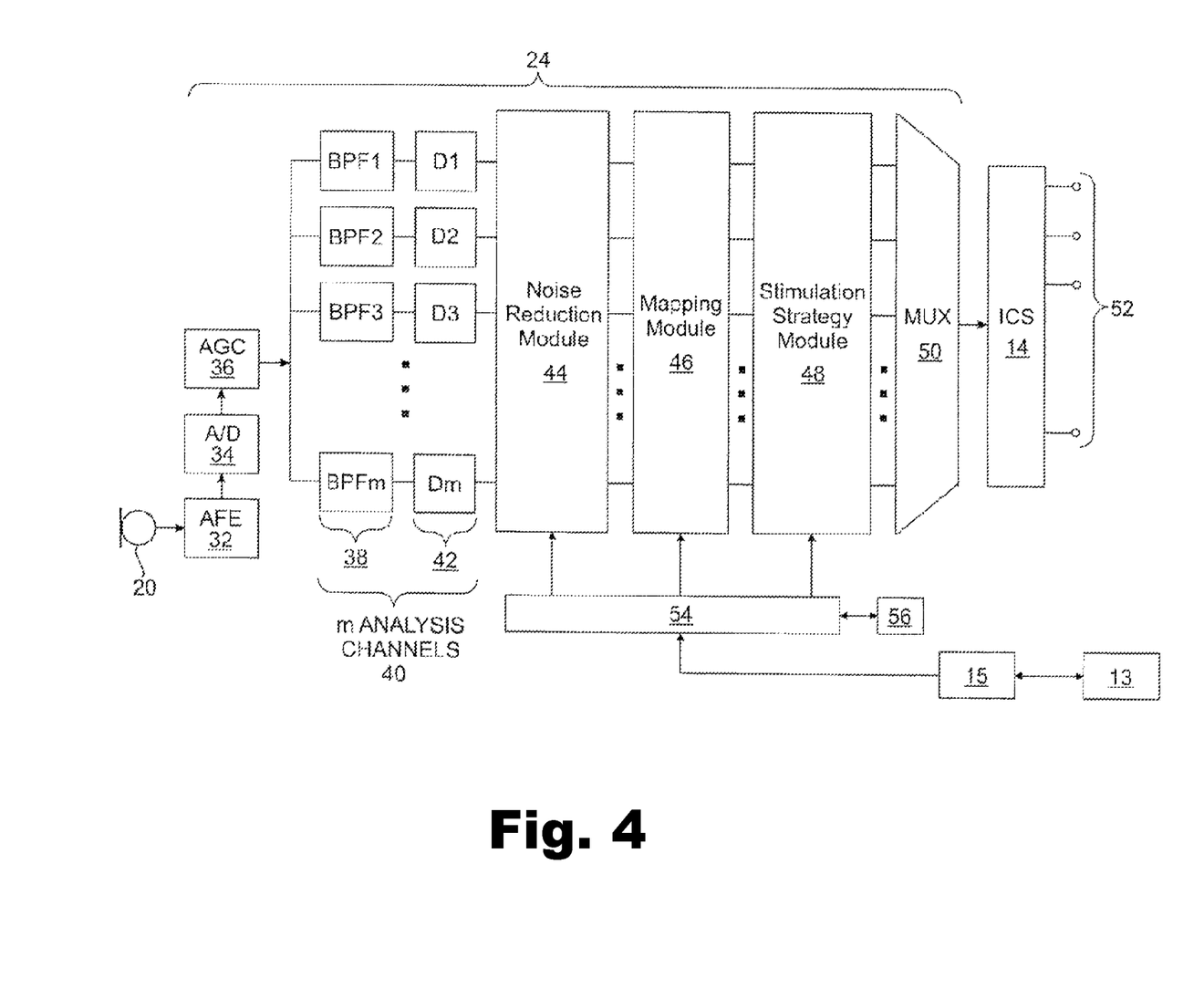
FIG. 4 is a block diagram of an example of the signal processing structure of a CI device according to principles described herein.

In FIG. 4 a schematic example of a sound processor 24 is shown. The audio signals captured by the microphone 20 are amplified in an audio front end circuitry 32, with the amplified audio signal being converted to a digital signal by an analog-to-digital converter 34. The resulting digital signal is then subjected to automatic gain control using a suitable automatic gain control (AGC) unit 36.

After appropriate automatic gain control, the digital signal is subjected to a filterbank 38 comprising a plurality of filters F1 . . . Fm (for example, band-pass filters) which are configured to divide the digital signal into m analysis channels 40, each containing a signal representative of a distinct frequency portion of the audio signal sensed by the microphone 20. For example, such frequency filtering may be implemented by applying a Discrete Fourier Transform to the audio signal and then distribute the resulting frequency bins across the analysis channels 40.

The signals within each analysis channel 40 are input into an envelope detector 42 in order to determine the amount of energy contained within each of the signals within the analysis channels 40 and to estimate the noise within each channel. After envelope detection the signals within the analysis channels 40 may be input into a noise reduction module 44, wherein the signals are treated in a manner so as to reduce noise in the signal in order to enhance, for example, the intelligibility of speech by the patient. Examples of the noise reduction module 44 are described in WO 2011/032021 A1.

The optionally noise reduced signals are supplied to a mapping module 46 which serves to map the signals in the analysis channels 40 to the stimulation channels S1 . . . Sn. For example, signal levels of the noise reduced signals may be mapped to amplitude values used to define the electrical stimulation pulses that are applied to the patient 17 by the ICS 14 via M stimulation channels 52. For example, each of the m stimulation channels 52 may be associated to one of the stimulation contacts 19 or to a group of the stimulation contacts 19.

The sound processor 24 further comprises a stimulation strategy module 48 which serves to generate one or more stimulation parameters based on the noise reduced signals and in accordance with a certain stimulation strategy (which may be selected from a plurality of stimulation strategies). For example, stimulation strategy module 48 may generate stimulation parameters which direct the ICS 14 to generate and concurrently apply weighted stimulation current via a plurality 52 of the stimulation channels S1 . . . Sn in order to effectuate a current steering stimulation strategy. Additionally or alternatively the stimulation strategy module 48 may be configured to generate stimulation parameters which direct the ICS 14 to apply electrical stimulation via only a subset N of the stimulation channels 52 in order to effectuate an N-of-M stimulation strategy.

The sound processor 24 also comprises a multiplexer 50 which serves to serialize the stimulation parameters generated by the stimulation strategy module 48 so that they can be transmitted to the ICS 14 via the communication link 30, i.e. via the coil 28.

The sound processor 24 may operate in accordance with at least one control parameter which is set by a control unit 54. Such control parameters, which may be stored in a memory 56, may be the most comfortable listening current levels (MCL), also referred to as "M levels", threshold current levels (also referred to as "T levels"), dynamic range parameters, channel acoustic gain parameters, front and back end dynamic range parameters, current steering parameters, amplitude values, pulse rate values, pulse width values, polarity values, the respective frequency range assigned to each electrode and/or filter characteristics. Examples of such auditory prosthesis devices, as described so far, can be found, for example, in WO 2011/032021 A1.

The programming unit 13 may act on the control unit 54 via the interface 15 for causing the ICS 14 and the electrode array 19 to apply a certain probe stimulus to the cochlea 200 as will be discussed in detail below.

The hearing aid 21 comprises a microphone arrangement 29 for capturing audio signals from ambient sound, an audio signal processing unit 27 for processing the captured audio signals and the loudspeaker 23 to which the processed audio signals are supplied to. The programming unit 13 may act, via the interface 15, on the audio signal processing unit 27 in order to cause the loudspeaker 23 to emit probe signals to be supplied to the contralateral ear.

Further, the programming unit 13 may adjust the respective stimulation parameters via the interface 15 in order to change, for examples the I/O curves of the CI device 10 and the hearing aid 21.

Figure 5:
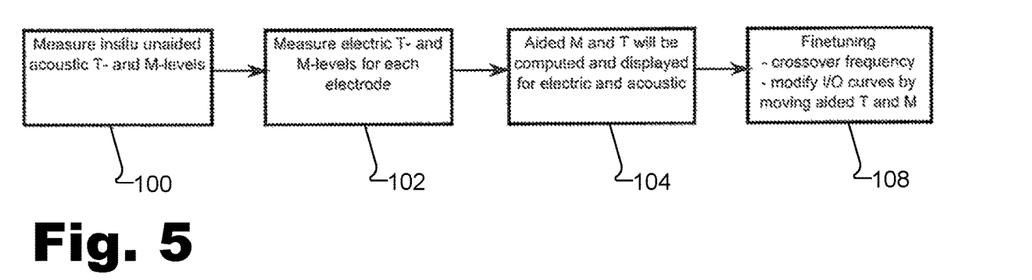
FIG. 5 is an example of a workflow of a method for fitting a bimodal system according to principles described herein.

FIG. 5 shows an example of a workflow for fitting of a bimodal stimulation system, such as the system of FIG. 1 comprising a CI device 10 and a hearing aid 21.

In a first step 100 appropriate hearing levels are empirically determined which characterize the residual hearing of the patient (residual hearing typically is present at relatively low frequencies, such as below 2 kHz), such as the hearing threshold level, the most comfortable level and/or the uncomfortable level. Such "unaided" levels are determined for various frequencies or frequency bands by presenting test sound at a certain level and at frequency/frequency band to the patient in order to obtain a certain behavioral feedback by the patient to the acoustic stimulation.

The hearing threshold level ("T-level") corresponds to the minimum sound level at which the hearing perception at a given frequency starts; the most comfortable level ("M-level") corresponds to the sound level which is perceived as being most comfortable at the respective frequency; and the uncomfortable level ("U-level") is the sound level at which the sound perception at the respective frequency starts to become uncomfortable. In some examples, the measurement of the unaided levels is done in-situ, i.e. with the patient wearing the hearing aid 21 and with the fitting device 13 controlling the sound processor 27 of the hearing aid 21 in a manner so as to generate and present appropriate test sound signals via the hearing aid loudspeaker 23 to the patient. In some examples, all three levels (i.e. T, M and U) are measured, but in some cases one may consider to measure only two of them, in particular T and M, or the T-level only.

Typically, such T-, M- and U-levels are given in "dB HL" (dB hearing level), i.e. dB relative to the level of the quietest sound a normal hearing person is able to perceive at a given frequency. Alternatively, T-, M- and U-levels may be given in "dB SPL" (dB sound pressure level) at the ear drum or free-field (in this case, the level is not related to the perception of the normal hearing person).

In step 102, the sensitivity of the patient's hearing with regard to electric stimulation is empirically evaluated, in particular by measuring the required current level applied to a certain electrode of the CI device 10 in order to achieve the respective hearing perception; typically, these levels will be the hearing threshold current level (i.e. the minimum level of the current to be applied to the respective electrode in order to create a hearing sensation by the patient), the most comfortable current level (i.e. the current level at which the most comfortable hearing impression is created), and/or the uncomfortable current level (i.e. the current level at which the hearing impression starts to become uncomfortable). The respective levels are determined for each electrode. The required probe current signal is generated by the fitting device 13 which controls the CI device 10 accordingly. Typically, the current level measurements require behavioral feedback by the patient. However, in principle it is also possible to determine at least the T-levels by objective measurements (such as electrically evoked compound action potential (ECAP), neural response imaging (NRI) and auditory brainstem, response (ABR)), wherein the neural response to the current stimulus is detected, typically by back-telemetry; optionally, M-levels may be determined via eSRT (electrically evoked stapedius reflex threshold) measurements.

It is to be understood that, while embodiments of the systems and methods described herein relate to electric stimulation of the cochlea via an electrode array implanted within the cochlea, the systems and methods described herein also may be applied to other kinds of neural stimulation, such as optical stimulation via optical fibers implanted within the cochlea. Thus, the above-mentioned electrical stimulation signal (stimulation current) is to be understood only as a specific example of a general neural stimulation signal. It is also to be understood that a stimulation electrode of an electrode array is only a specific example of a stimulation channel which, in the case of optical stimulation, may be represented by one of several light emission areas in the cochlea.

The unaided acoustic stimulation levels determined in step 100 and the electric stimulation levels determined in step 102 are stored in a memory of the fitting device 13; alternatively or in addition, these levels also may be stored in the hearing aid 21 and the CI device 10, respectively.

In general, as already mentioned above, signal processing in a hearing stimulation device occurs according to a certain "stimulation model" including a set of stimulation parameters. In relatively simple cases the stimulation model may be described on the base of I/O curves; for acoustic stimulation, a separate I/O curve may be provided for each input frequency band, and for electric stimulation, a separate I/O curve may be provided for each electrode. More complex stimulation models may include frequency manipulation, such as frequency shifting and/or frequency compression, both for acoustic and electric stimulation, and simultaneous stimulation of adjacent electrodes ("current steering", wherein e.g. two adjacent electrodes may be stimulated in order to achieve a pitch in-between the pitches attributed to the electrodes). The stimulation model may include an auditory model for taking into account effects like spread of excitation and masking.

Figure 6:
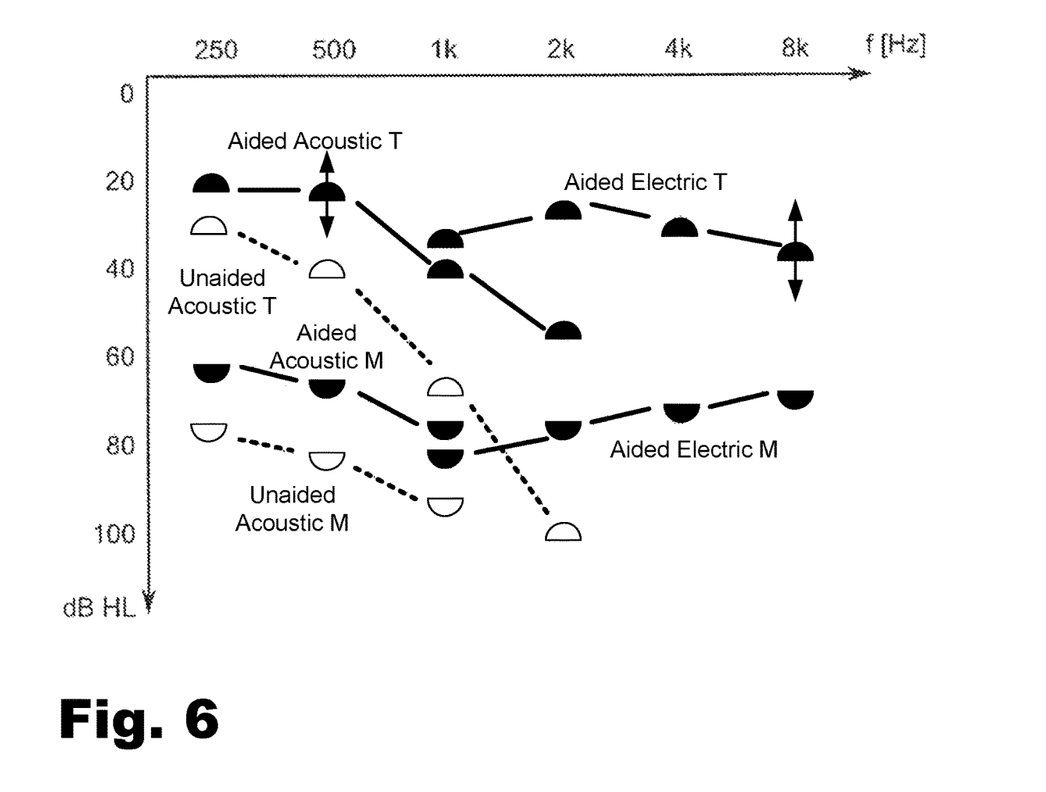
FIG. 6 is an example of an acoustic level audiogram representation of the hearing threshold levels and most comfortable levels of a bimodal stimulation system, as shown by a graphical user interface of a fitting device according to principles described herein.

In step 104 the unaided acoustic stimulation levels of step 100 and the electric stimulation levels of step 102 are used to calculate, by taking into account the respective stimulation model including the presently set values of stimulation parameters, such as I/O curves of the acoustic stimulation in the hearing aid 21 and the electrical stimulation in the CI device 10, the respective "aided" acoustic stimulation levels and the respective "aided" electric stimulation levels; the calculated aided levels then are displayed on the graphical user interface (such as a screen 31) of the fitting device 15 in an aided audiogram representation as shown in FIG. 6. For the acoustic stimulation, such calculation may be performed for various audiometric frequencies which may equal the frequencies or frequency bands for which the respective unaided levels are known; alternatively or in addition, such calculation may be performed for other audiometric frequencies by appropriate interpolation. For the electric stimulation, such calculation may be performed for the audiometric frequencies corresponding the center frequency of each electrode; however, such calculation may be performed also for audiometric frequencies in-between the center frequencies of the electrodes.

Figure 7A:
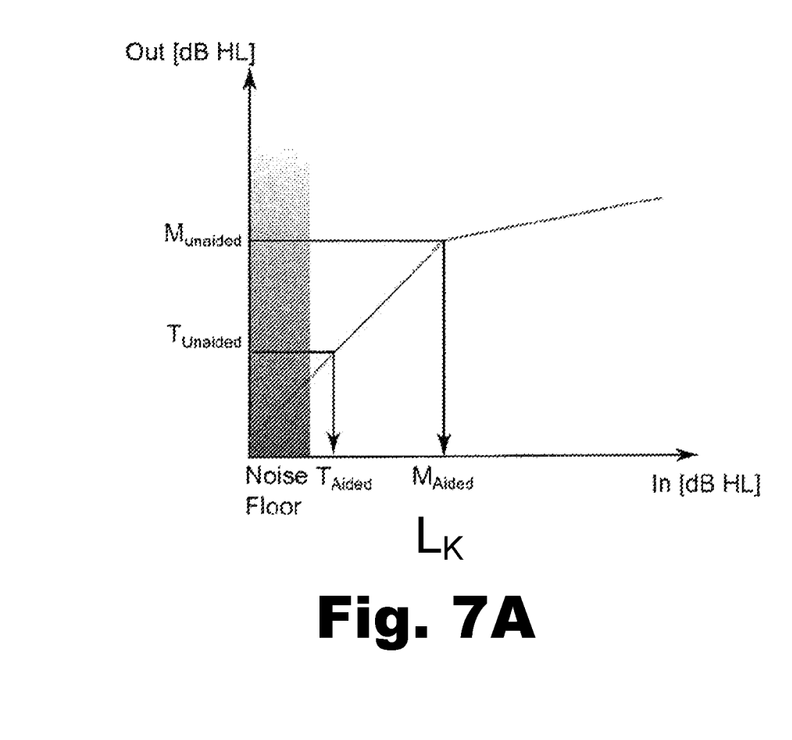
FIGS. 7A and 7B are examples of an I/O curve of the acoustic stimulation device of a bimodal stimulation device and an I/O curve of the electric stimulation device of the bimodal stimulation device, respectively, according to principles described herein.
Figure 7B:
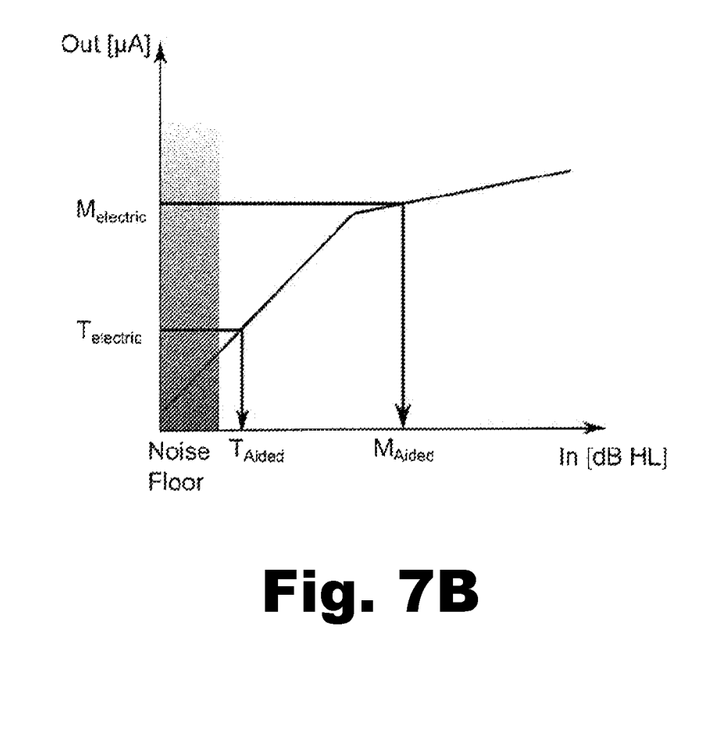

Examples for I/O curves for acoustic stimulation by the hearing aid 21 and electric stimulation by the CI device 10 are shown in FIGS. 7A and 7B, respectively. An I/O curve for acoustic stimulation represents the level of the sound output provided by the loudspeaker 23 (typically given in dB HL) as a function of the sound level to which the microphone 29 of the hearing aid 21 is exposed to (typically also given in dB HL). An I/O curve for electric stimulation represents the stimulation current applied to the respective electrode as a function of the sound level to which the microphone of the CI device is exposed (typically given in dB HL). There is a separate I/O curve for each stimulation channel (i.e. for each stimulation electrode).

In general, there are adjustable/variable contributions (namely the signal processing parameters which are adjustable by the fitting procedure) and non-adjustable contributions to the I/O curves.

For example, for the hearing aid 21, the primary adjustable contributions are the gain applied in the linear (i.e. non-compressed) range up to the knee-point input level $L_K$ at which compression starts, the compression ratio applied for input levels above $L_K$, and the value of $L_K$. The main non-adjustable contributions are the sensitivity of the microphone 29, the noise floor of the input stage (noise of microphone and noise of analog to digital converter) and the type and coupling of the receiver 23 to the ear canal.

For electric stimulation, the adjustable parameters are all fitting parameters which affect the "mapping function", such as the sensitivity of the CI device (at low sensitivity, close sound is more desirable over remote sound than at high sensitivity), the input level at which the AGC turns on/off, the input dynamic range (IDR) (the IDR of a CI sound processor is the ratio between the loudest and softest sounds that will be presented by the CI device to the patient), the "technical T-level" and the "technical M-level". The technical T-level denotes the stimulation current applied at very low input levels; and the technical M-level denotes the stimulation current applied at the input level at the knee-point in the curve of FIG. 7B (however, it is to be noted that these "technical" T and M-levels are not the same as the electric T- and M-levels measured in step 102 which are indicated at "$T_{electric}$" and "$M_{electric}$" in FIG. 7B (and which may also be labeled "behavioral T-level" and "behavioral M-level")); the technical T- and M-levels typically differ slightly from the hearing threshold current level and the most comfortable current level determined in step 102 for an optimized fitting of the CI device 10. The main non-adjustable contributions to the I/O curves of electric stimulation are the sensitivity of the microphone 20 and the coupling of the respective electrode 18 to the auditory nerve.

For the non-adjustable contributions of the initially used I/O curves (i.e. the I/O curves forming the starting point of the fitting process) one may use default values known for the respective hearing aid type and CI device type. However, accuracy of the initial I/O curves may be enhanced by conducting technical measurements concerning the actual microphone sensitivities and the actual electrode currents (electrode currents may be measured via back-telemetry) utilizing the fitting device 13 in order to replace the respective default values by individually determined empirical values. In other words, generally at least part of the initially used stimulation parameters may be set to default values.

According to one example, for the initially used I/O curves not only the non-adjustable contributions but also the adjustable contributions may be set according to default values which are specific to the respective type of hearing aid and CI device (i.e., according to one example, all of the initially used stimulation parameters may be set to default values).

According to an alternative embodiment, initially the adjustable stimulation parameters (such as the adjustable parameters of the initially used I/O curves) may be set according to values calculated based on the unaided levels determined in step 100 and the electric levels determined in step 102. For example, for acoustic stimulations such "pre-calculation" of the fitting parameters may be based on the usual prescription fitting formulas, such as NAL-NL1, etc. For electric stimulation, the pre-calculation may provide for an empirical estimation of how much the fitting parameters "technical T-level" and the "technical M-level" may differ from the hearing threshold current level "$T_{electric}$" and the most comfortable current level "$M_{electric}$" determined in step 102; for example, according to a default setting without pre-calculation, these differences could be set to zero. In general, the "pre-calculation" of the I/O curves should advance the initially used I/O curves as close as possible towards the optimal I/O curves in order to shorten the (manual) fitting procedure.

The arrows in FIG. 7A show schematically how the aided T-level is determined from the unaided T-level by taking into account the I/O curve of the respective frequency channel (or a combination of channels, e.g. if the audiometric frequency is in the middle between two adjacent filters): the aided T-level is that value of the input level which is associated, via the I/O curve, with an output level which has the value of the unaided T-level. The same procedure applies to the respective M-levels (and U-levels). In the most simple case, the aided electric levels may be determined in the same manner as for the acoustic stimulation in FIG. 7A, as indicated by the dashed arrows in FIG. 7B, i.e. the aided electric T-level "$T_{aided}$" is that value of the input level which is associated, via the I/O curve, with an output current which has the value of the measured behavioral T-level "$T_{electric}$".

However, as already mentioned above, more sophisticated calculations may take into account an appropriate auditory model based on the selected coding strategy, in order to take into account, for example, the impact of overlapping electric fields at adjacent electrodes and refractory effects on loudness. Such auditory model may take into account the result of objective measurements (such as ECAP, NRI, eSRT and/or ABR) in order to estimate, for example, the spread of excitation inside the cochlea.

The aided acoustic and electric levels are shown in a common acoustic level audiogram representation as a function of the audiometric frequency, with the levels being given for both acoustic stimulation and electric stimulation in an acoustic level unit (in example of FIG. 6, the unit is "dB HL"), so that the aided electric levels are directly comparable to the aided acoustic levels; further, the aided levels for electric and acoustic stimulation are fully comparable not only with regard to the level value, but also with regard to frequency, since also the aided electric stimulation levels are shown as a function of frequency, like the aided acoustic stimulation levels (to this end, the frequency allocation of the stimulation channels/electrodes is used).

In the example of FIG. 6, the aided electric and acoustic T-levels and M-levels are shown. Typically, for EAS patients acoustic stimulation takes place at relatively low frequencies, such as below 1 kHz, and electric stimulation takes place at higher frequencies, such as above 1 kHz (a typical start frequency for electric stimulation is around 200 Hz and is not changed for patients with electric stimulation at one ear and acoustic stimulation at the other ear; for EAS patients the electric start frequency may be increased regularly). According to an embodiment, there may be a distinct crossover frequency which separates acoustic stimulation from electric stimulation; according to an alternative embodiment, there may be an overlapping frequency range in which both acoustic and electric stimulation may take place.

According to the example of FIG. 6, the unaided levels determined in step 100 may be shown together with the calculated aided levels, or they may be shown in an alternating manner with regard to the calculated aided levels. Further, normal hearing curves may be shown together with or alternatingly with other curves on the graphical user interface. Typically, the user will be allowed to select which curves are displayed. In particular, there may be a representation in which the aided electric levels are shown only, and there may be a representation in which the aided acoustic levels are shown only, in addition to the common representation in the example of FIG. 6, wherein both aided electric and acoustic levels are shown on the same screen.

While in the example of FIG. 6 the common level unit is "dB HL" for acoustic and electric stimulation, as an alternative the selected unit may be "dB SPL at ear drum" or "dB SPL free-field"; in some examples, the presently used unit may be selectable by the user.

The user may interact with the graphical user interface in a manner so as to adjust the aided levels, for example by "drag-and-drop-action" on the respective symbol, i.e. the symbols may be manually shifted vertically upwards or downwards in order to increase or decrease the respective aided level. This applies both to the acoustic and the electric levels. Upon such adjustment of the respective aided level, the fitting device 13 will adjust the values of the stimulation parameters (such as the respective I/O curve) in conformity with the aided level adjustment so as to accordingly adjust the respective stimulation device, i.e. the hearing aid 21 or the CI device 10. In other words, adjustment of the aided level by the audiologist causes a corresponding adjustment of the stimulation parameters (such as the adjustable parameters of the respective I/O curve).

For example, when an aided electric T-level is manually increased (see arrows in FIG. 6), the respective I/O curve in FIG. 7B is changed in such a manner that the current levels at low input levels are increased, thus making the CI device 10 more sensitive at low input levels of the respective frequency band/electrode.

Similarly, when an aided acoustic T-level is manually increased, the gain of the respective I/O curve may be increased accordingly.

According to one example, the audiogram representation of FIG. 6 may include a marked area of audiometric frequencies and stimulation levels which are particularly important for speech understanding (also called "speech banana").

In some examples, the user interface allows adjustment of the bandwidth of the acoustic stimulation and the bandwidth of the electric stimulation by a manual adjustment of the respective frequency ranges. In particular, the graphical user interface may allow selection and adjustment of a crossover frequency between acoustic and electric stimulation.

The above-mentioned manual adjustment of the aided levels and the bandwidth/crossover frequency is shown as step 106 in the workflow of FIG. 5.

According to one embodiment, the fitting device 13 may be designed to allow behavioral measurements, with the patient both utilizing the hearing aid 21 and the CI device 10, in order to actually measure the aided electric and acoustic stimulation levels which have been previously calculated, so that the accuracy of the calculation can be evaluated. Such behavioral measurements may include loudness scaling (in a loudness scaling procedure, the patient has to assign a number of verbal categories, such as soft, very loud, etc., to a stimulus, such as an electric pulse train or acoustic narrowband noise, at different levels; the result is a loudness growth function). According to one option, deviations between the measured aided levels and the respective calculated aided levels may be automatically (or manually) compensated. According to another option, a warning may be issued by the fitting device 13 in case that the deviations between the measured aided levels and the respective calculated aided levels exceed a certain degree.

Alternatively or in addition, objective measurements (such as ECAP or NRI) may be used for electric stimulation in order to improve inaccuracy of the auditory models and thus the accuracy of the calculation of the aided levels.

While the above examples relate to fitting by visualization and adjustment of the T- and M-levels, it is to be understood that in some cases only one of the levels, in particular the T-level, may be visualized and adjusted, or that all three levels (T-, M- and U-levels) may be visualized and adjusted. In some examples, at least two of the three levels (T-, M- and U-levels) are visualized and adjusted.

While according to the examples described so far the first stimulation device may be a cochlear implant for electric stimulation of the (ipsilateral) cochlea, it could be, alternatively, any other device for neural hearing stimulation, such as cochlear implant for optical stimulation of the cochlea or an auditory brainstem implant.

As already mentioned above, the second stimulation device may be an acoustic stimulation device in the sense that it provides for vibrational stimulation of the ipsilateral and/or the contralateral ear; for example, the second stimulation device may be an electro-acoustic hearing aid comprising a loudspeaker as the output transducer, a bone conduction hearing aid, a middle ear implant (MEI) or a direct acoustic cochlea stimulator (DACS).

However, according to an alternative embodiment, the second stimulation device also may be neural stimulation device which, however, uses a stimulation mode different from that of the first stimulation device. In this regard, different stimulation modes use qualitatively or quantitatively different outputs. For example, if the first stimulation device is a cochlear implant for electric stimulation of the (ipsilateral) cochlea, second stimulation device may be a cochlear implant for optical stimulation of the (contralateral) cochlea (optical output rather than electric output) or an auditory brainstem implant (electric output of different magnitude, etc.).

It is to be understood that the audiometric frequency, i.e. the frequency in an audiogram representation, corresponds to the frequency/pitch resulting from a stimulus as perceived by the patient (for acoustic stimulation, the pitch corresponds to the vibration frequency of the output transducer; for electric stimulation the pitch primarily is determined by the current pattern (current levels of the electrodes) and the electrode positions, wherein an auditory model may be used to calculate/estimate the pitch (and the loudness) resulting from a certain stimulation current pattern). For example, the audiogram representation of an aided T-level at 1 kHz indicates the minimum level at which a 1 kHz (sine or narrowband) sound has to be presented to the patient wearing the stimulation device in order to create a hearing sensation. It is also to be understood that the audiometric frequency at which an aided level is given in the audiogram representation may be different from the center frequencies of the filterbanks used for dividing the input sound.

Figure 8:
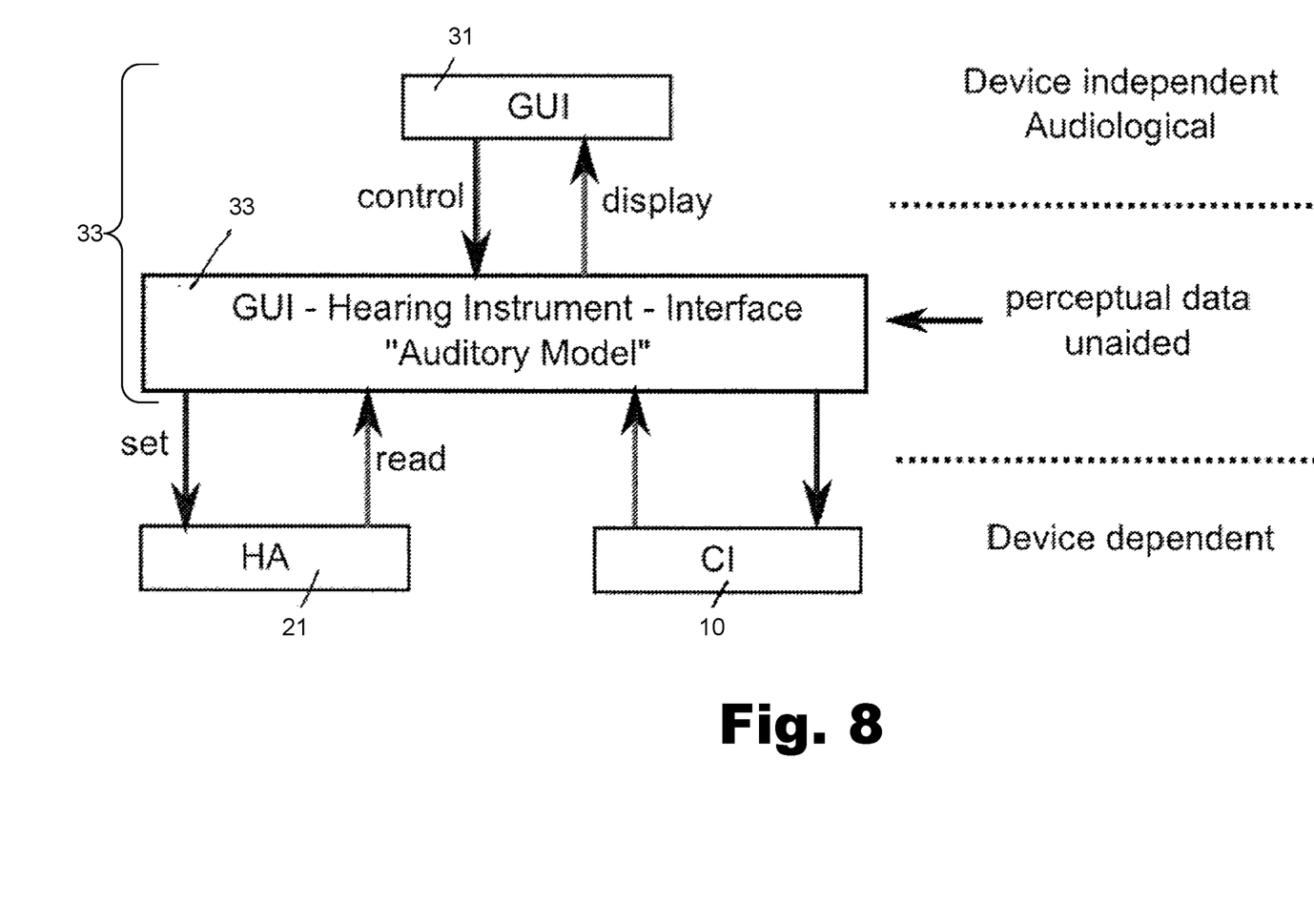
FIG. 8 is a schematic representation of an example of a system according to principles described herein.

In FIG. 8 a schematic representation of a fitting system architecture of the systems and methods described herein is shown, according to which a graphical user interface (GUI) 31 is connected via an "interface unit" 33 with the first stimulation device 10 and the second stimulation device 21. The unit 33 forms part of the fitting system and serves as an interface between the GUI 31 and the stimulation devices 10, 21 in a manner so as to render the GUI 31 independent from the stimulation devices 10, 21 in the sense that what is displayed on the GUI 31, such as the aided audiogram representation described above, is the same for all types of stimulation devices 10, 21, irrespective of which stimulation mode the respective stimulation device 10, 21 utilizes. The unit 33 functionally corresponds to a data processing unit which reads the presently set values of the stimulation parameters from the first stimulation device 10 and the second stimulation device 21 and then calculates the aided levels for the audiogram representation from these values, taking into account the respective stimulation model (which is implemented in the unit 33 for each type of stimulation device). The unaided levels for acoustic stimulation and the neural stimulation signal levels for neural stimulation may be read as well from the first stimulation device 10 and the second stimulation device 21 (if available on these devices), or they may be stored by the unit 33 (if supplied from another source). The results of the calculations are supplied to the GUI 31.

The audiologist may act on the GUI 31 so as to adjust the aided levels, which adjustment is supplied as input to the unit 33 which calculates the accordingly adjusted values of the stimulation parameters in order to set these adjusted values as the new values of the stimulation parameters in the first stimulation device 10 and the second stimulation device 21.

Figure 9:
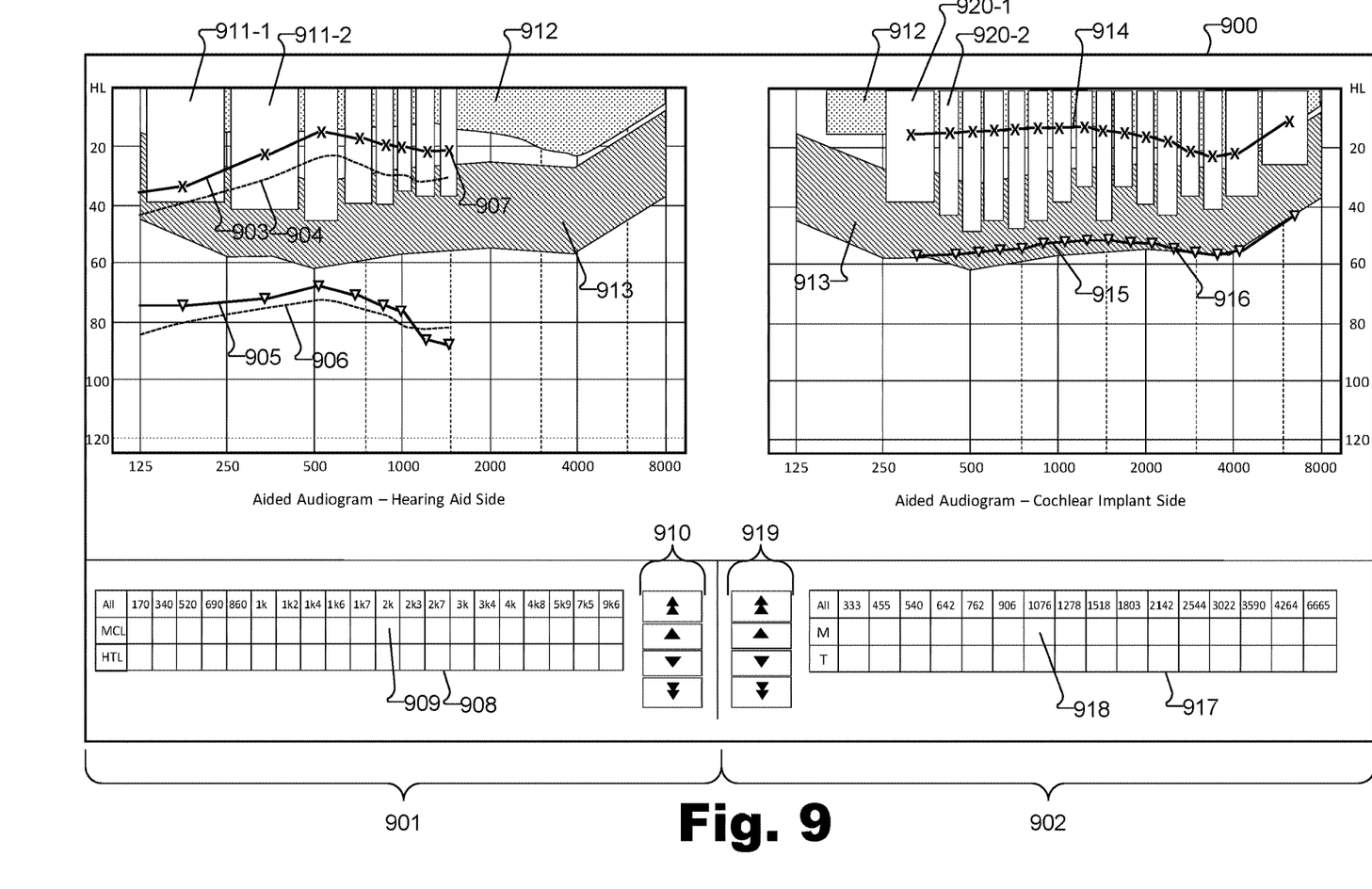
FIG. 9 is an exemplary graphical user interface that may be displayed by a fitting device according to principles described herein.

FIG. 9 illustrates another exemplary GUI 900 that may be displayed by a fitting device described herein. As shown, aided audiogram information for a hearing aid included in a bimodal hearing stimulation system is displayed on a hearing aid side 901 of GUI 900 and aided audiogram information for a cochlear implant included in the bimodal hearing stimulation system is displayed on a cochlear implant side 902 of GUI 900. In alternative embodiments, only the aided audiogram information for the hearing aid or only the aided audiogram information for the cochlear implant may be displayed at any given time.

As shown, an aided acoustic T-level curve 903 ("curve 903") representative of aided acoustic T-levels in dB HL across a frequency spectrum is displayed within GUI 900. The closer curve 903 is to 0 dB HL, the closer the patient's acoustic T-levels will be comparable to the acoustic T-levels of a normal hearing person. Curve 903 represents how incoming sounds relate to the patient's perceived audibility, after the hearing aid has processed these incoming sounds.

A target acoustic T-level curve 904 ("curve 904") representative of target acoustic T-levels across the frequency spectrum is also displayed within GUI 900. Curve 904 can be referred to as a "fitting target" and may be determined based on an unaided audiogram of the patient, statistical clinical data, and/or any other suitable data. Curve 904 may also be determined in accordance with various fitting formulas and/or fitting rationales, such as DSL and NAL. A user may compare curves 903 and 904 and get an idea of where curve 903 might need to be adjusted in order to select proper T-levels for the patient.

An aided acoustic M-level curve 905 ("curve 905") representative of aided acoustic M-levels in dB HL across the frequency spectrum is also displayed within GUI 900. Curve 905 shows the levels at the processed frequencies at which the patient perceives a presented signal as "comfortable". Curve 905 illustrates how incoming sounds relate to the patient's comfortable sound perception, after the hearing aid has processed these incoming sounds.

A target acoustic M-level curve 906 ("curve 906") representative of target acoustic M-levels across the frequency spectrum is also displayed within GUI 900. Curve 906 can be referred to as a "fitting target" and may be determined based on an unaided audiogram of the patient, statistical clinical data, and/or any other suitable data. Curve 906 may also be determined in accordance with various fitting formulas and/or fitting rationales, such as DSL and NAL. A user may compare curves 905 and 906 get and get an idea of where curve 905 might need to be adjusted in order to select proper M-levels for the patient.

Aided acoustic T-levels and M-levels may be adjusted by a user via GUI 900 in any suitable manner. For example, a user may interact directly with curves 903 and/or 905 and adjust them to adjust the aided acoustic T- and M-levels (and therefore the unaided acoustic T- and M-levels for the patient). For example, a user can select a point (e.g., point 907) along one of curves 903 or 905 and drag the point up or down to adjust the value of the corresponding aided acoustic T- or M-level for the frequency that corresponds to the point.

Additionally or alternatively, a user can select an appropriate cell within a selection matrix 908 to adjust a particular aided acoustic T- or M-level. For example, to adjust an aided acoustic M-level at a frequency of 2 kHz, the user may select cell 909 and the adjust the value up or down using one or more of arrow buttons 910.

To aid the user in adjusting the aided acoustic T- and M-levels, other information may be presented within GUI 900. For example, spectrum analyzer bars 911 (e.g., bars 911-1 and 911-2) representative of signal levels of signals detected by a microphone of the hearing aid may be presented within GUI 900. The signal levels may be directly measured on the microphone of the hearing aid and converted into the audiogram level (linear transform from sound pressure levels). Bars 911 may be dynamically updated in real-time (e.g., "dancing bars") as the signal levels change.

By displaying bars 911 within the same GUI 900 as curves 903-906, the user may readily ascertain how the aided acoustic T- and M-levels compare with the signal levels of signals detected by the microphone.

A graphical representation of a noise floor 912 of the hearing aid may also be displayed within GUI 900, as shown in FIG. 9. By displaying noise floor 912, the fitting device may assist the user in avoiding adjusting the aided acoustic T-levels into the noise floor 912.

A graphical representation of a speech banana 913 may also be displayed within GUI 900, as shown in FIG. 9. Speech banana 913 is a representation of the usual frequency range (left to right) and level range (up and down) of average spoken speech. In some examples, a user may attempt to adjust the aided acoustic M-levels to be within the speech banana 913. Similar information may be displayed on the cochlear implant side 902. For example, as shown, an aided electric T-level curve 914 ("curve 914") representative of aided electric T-levels in dB HL across a frequency spectrum is displayed within GUI 900. The closer curve 914 is to 0 dB HL, the closer the patient's electric T-levels will be comparable to the electric T-levels of a normal hearing person. Curve 914 represents how incoming sounds relate to the patient's perceived audibility, after the cochlear implant has processed these incoming sounds.

An aided electric M-level curve 915 ("curve 915") representative of aided electric M-levels in dB HL across the frequency spectrum is also displayed within GUI 900. Curve 915 shows the levels at the processed frequencies at which the patient perceives a signal presented by the cochlear implant as "comfortable". Curve 915 illustrates how incoming sounds relate to the patient's comfortable sound perception, after the cochlear implant has processed these incoming sounds.

Aided electric T-levels and M-levels may be adjusted by a user via GUI 900 in any suitable manner. For example, a user may interact directly with curves 914 and/or 915 and adjust them to adjust the aided electric T- and M-levels (and therefore the unaided electric T- and M-levels for the patient). For example, a user can select a point (e.g., point 916) along one of curves 914 or 915 and drag the point up or down to adjust the value of the corresponding aided electric T- or M-level for the frequency that corresponds to the point.

Additionally or alternatively, a user can select an appropriate cell within a selection matrix 917 to adjust a particular aided electric T- or M-level. For example, to adjust an aided electric M-level at a frequency of 1076 Hz, the user may select cell 918 and the adjust the value up or down using one or more of arrow buttons 919.

While not shown in FIG. 9, target electric T-level and/or M-level curves may also be displayed within GUI 900. These target curves may be similar to the target acoustic curves 904 and 906, and may be determined in accordance with various fitting formulas and/or fitting rationales.

To aid the user in adjusting the aided electric T- and M-levels, other information may be presented within GUI 900. For example, spectrum analyzer bars 920 (e.g., bars 920-1 and 920-2) representative of signal levels of signals detected by a microphone of the cochlear implant may be presented within GUI 900. The signal levels may be directly measured on the microphone of the cochlear implant and converted into the audiogram level (linear transform from sound pressure levels). Bars 920 may be dynamically updated in real-time (e.g., "dancing bars") as the signal levels change. By displaying bars 920 within the same GUI 900 as curves 914 and 915, the user may readily ascertain how the aided electric T- and M-levels compare with the signal levels of signals detected by the microphone.

The initial values for aided acoustic T-level curve 903, aided acoustic M-level curve 905, aided electric T-level curve 914, and aided electric M-level curve 915 (i.e., the initial aided behavioral values) may be set in any suitable manner. For example, the initial aided behavioral values may be set by measuring unaided behavioral values for the specific patient and converting the unaided behavioral values into the initial aided behavioral values in any of the ways described herein. If measurement data is not available, the initial aided behavioral values may be determined by estimating the unaided behavioral values.

For example, the fitting device may estimate the unaided acoustic T-levels based on hearing aid gain (e.g., via a half-gain-rule) and the unaided acoustic M-levels based on statistical data (e.g., Pascoe) based on an unaided threshold. The estimated unaided acoustic T- and M-levels may then be converted into the initial aided acoustic T- and M-levels.

As another example, the fitting device may estimate the unaided electric T- and M-levels based on the most recent stimulation values changed while the cochlear implant is operating in an internal stimulation mode. As used herein, an internal stimulation mode refers to a mode in which the cochlear implant applies a specific pulse pattern that is completely independent of an external audio signal detected by the cochlear implant microphone. For example, one type of internal stimulation mode is a tone burst mode wherein a stimulation pattern is applied via a single electrode. Another type of internal stimulation mode is a speech burst mode wherein a stimulation pattern is concurrently applied via a plurality of electrodes. If these values are not available, the fitting device may use the unaided electric M-levels as currently used by the cochlear implant and calculate the unaided electric T-levels as a fixed percentage (e.g., 28 percent) of the unaided electric M-levels. The estimated unaided electric T- and M-levels may then be converted into the initial aided electric T- and M-levels.

In some examples, the fitting device may be configured to automatically calibrate any of the information displayed in GUI 900 to compensate for a change in microphone sensitivity. Such change may be caused by microphone blockage, for example. To this end, the fitting device may provide sound to a hearing device (e.g., a hearing aid or cochlear implant) having a particular sound level (e.g., 65 dB SPL). The fitting device may measure (or direct the hearing device to measure) a sound level of the signal detected by the microphone. If the detected sound level is different than the input sound level, one or more of the curves displayed in GUI may be adjusted accordingly.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a first stimulation device for neural stimulation of a patient's ipsilateral ear;
a second stimulation device for stimulation of the patient's contralateral ear, wherein a stimulation mode of the second stimulation device is different from a stimulation mode of the first stimulation device; and
a fitting device configured to be communicatively connected to the first and second stimulation device for adjusting the first stimulation device and the second stimulation device;
the first stimulation device comprising
an implantable neural stimulation arrangement comprising a plurality of stimulation channels for neural stimulation of the ipsilateral ear at various stimulation sites according to a neural stimulation signal; and
a sound processor for generating the neural stimulation signal for each stimulation channel from an input audio signal according to a neural stimulation model including a first set of stimulation parameters;
the second stimulation device comprising
an audio signal processing unit for generating a stimulation signal from the input audio signal according to a stimulation model including a second set of stimulation parameters; and
an output transducer for stimulation of the contralateral ear according to the stimulation signal,
the system further comprising a memory for storing, for at least some of the stimulation channels, at least one of a hearing threshold neural stimulation signal level, a most comfortable neural stimulation signal level and an uncomfortable neural stimulation signal level;
the fitting device comprising
a data processing unit
for calculating, for at least some audiometric frequencies, at least one of an aided hearing threshold level, an aided most comfortable level and an aided uncomfortable level by taking into account the stimulation model of the second stimulation device and using the values of the second set of stimulation parameters as read from the second stimulation device, and
for calculating, for the at least some audiometric frequencies, at least one of an aided hearing threshold level, an aided most comfortable level and an aided uncomfortable level from the stored hearing threshold neural stimulation signal level, most comfortable neural stimulation signal level and uncomfortable stimulation neural stimulation signal level by taking into account the stimulation model of the first stimulation device using the values of the first set of stimulation parameters as read from the first stimulation device; and
a graphical user interface configured to present an acoustic level audiogram representation of the calculated at least one of the aided hearing threshold level, the aided most comfortable level and the aided uncomfortable level as a function of the audiometric frequency both for neural stimulation by the first stimulation device and for stimulation by the second stimulation device.

2. The system of claim 1, wherein the first stimulation device is a cochlear implant for electric stimulation of the ipsilateral cochlea, the cochlear implant stimulation arrangement comprising an electrode array, and wherein the neural stimulation signal is an electrode stimulation current.

3. The system of claim 1, wherein the second stimulation device is for acoustic stimulation within an acoustic stimulation frequency range, wherein the stimulation signal is an acoustic stimulation signal, wherein the output transducer is for generating a vibration output according to the acoustic stimulation signal; wherein the memory is for storing, for at least some frequency bands of an input audio signal, at least one of an unaided hearing threshold level, an unaided most comfortable level and an unaided uncomfortable level, wherein the data processing unit is for calculating, for at least some audiometric frequencies within the acoustic stimulation frequency range said at least one of an aided hearing threshold level, an aided most comfortable level and an aided uncomfortable level from the stored unaided levels.

4. The system of claim 3, wherein the graphical user interface is configured to enable selection of a crossover frequency by the user, the crossover frequency separating acoustic and neural stimulation in that at frequencies below the crossover frequency stimulation is to take place by the second stimulation device only and that at frequencies above the crossover frequency stimulation is to take place by the first stimulation device only.

5. The system of claim 3, wherein the fitting device is configured to cause the second stimulation device to present acoustic test stimulation signals to the patient, and wherein the fitting device is configured to record a perceptual behavioral response of the patient to such acoustic test stimulation signals in order to determine said at least one of the unaided hearing threshold level, the unaided most comfortable level and the unaided uncomfortable level as a function of the frequency of the acoustic test stimulation signals.

6. The system of claim 1, wherein the graphical user interface is configured to enable adjustment, in the aided audiogram representation by a user, of the values of the aided hearing threshold levels, the aided most comfortable levels and the aided uncomfortable levels for both for stimulation by the first stimulation device and for stimulation by the second stimulation device, wherein the fitting device is configured to adjust the stimulation parameters of the first and second stimulation devices in conformity with such aided level adjustment by the user, so as to accordingly adjust the first and second stimulation devices.

7. The system of claim 6, wherein the fitting device is configured to initially set at least part of the values of the stimulation parameters of the first and second stimulation devices according to default values which are specific to the type of the first and the type of the second stimulation device, with the initially set values of the stimulation parameters being adjustable via said user adjustment of the values of the aided hearing threshold levels, the aided most comfortable levels and the aided uncomfortable levels in the aided audiogram representation.

8. The system of claim 1, wherein the graphical user interface is configured to present the aided hearing threshold levels, the aided most comfortable levels and the aided uncomfortable levels for both the first stimulation device and the second stimulation device in a common audiogram representation.

9. The system of claim 8, wherein the graphical user interface is configured to allow the user to change, by user input, between the common audiogram representation and separate audiogram representations for the first stimulation device and the second stimulation device.

10. The system of claim 1, wherein the graphical user interface is configured to present at least the aided hearing threshold levels for both the first stimulation device and the second stimulation device.

11. The system of claim 1, wherein the fitting device is configured to cause the first stimulation device to present neural test stimulation signals to the patient, and wherein the fitting device is configured to record a perceptual behavioral response of the patient to such neural test stimulation signals in order to determine, for at least some of the stimulation channels, said at least one of the hearing threshold neural stimulation signal level, the most comfortable neural stimulation signal level and the uncomfortable neural stimulation signal level.

12. The system of claim 1, wherein the system comprises a loudspeaker for presenting test sounds to the patient, the test sounds being produced from test audio signals generated by the fitting device and supplied to the loudspeaker, and wherein the fitting device is configured to record a perceptual behavioral response of the patient to such test sounds when wearing and using the first and second stimulation device.

13. The system of claim 12, wherein the fitting device is configured to determine from the recorded perceptual behavioral response of the patient to the test sound at least one of a measured aided hearing threshold level, a measured aided most comfortable level and a measured aided uncomfortable level at least for at least some audiometric frequencies, and the fitting device is configured to compare each measured aided level to the calculated aided levels.

14. The system of claim 13, wherein the fitting device is configured to adjust the stimulation parameters of the first and second stimulation device in order to compensate for deviations between the measured aided levels and the calculated aided levels so as to make the calculated aided levels match with the measured aided levels.

15. The system of claim 14, wherein the fitting device is configured to issue a warning in case that the deviations between the measured aided levels and the calculated aided levels exceed a certain degree.

16. The system of claim 1, wherein the fitting device is configured to calculate the aided levels for the acoustic stimulation and for the neural stimulation by taking into account measured microphone sensitivity data of microphones of the first and second stimulation devices.

17. The system of claim 1, wherein the graphical user interface is further configured to present spectrum analyzer bars representative of signal levels of signals detected by at least one of a microphone of the first stimulation device and a microphone of the second stimulation device.

18. The system of claim 1, wherein the graphical user interface is further configured to present one or more target acoustic behavioral curves based on at least one a fitting formula and a fitting rationale.

19. The system of claim 1, wherein the fitting device is configured to calculate the aided levels for the acoustic stimulation and for the neural stimulation based on estimated non-aided levels for the acoustic stimulation and for the neural stimulation.

20. The system of claim 19, wherein the fitting device is configured to estimate the non-aided levels for the acoustic stimulation based on gain from the second stimulation device and statistical data.

21. The system of claim 19, wherein the fitting device is configured to estimate the non-aided levels for the electric stimulation based on values changed in tone burst or speech burst mode of the first stimulation device.

22. The system of claim 1, wherein the fitting device is configured to calibrate the aided levels for the acoustic stimulation and for the neural stimulation in response to a change in microphone sensitivity data of microphones of the first and second stimulation devices.

23. A method for fitting a first stimulation device for neural stimulation of a cochlea of a patient's ipsilateral ear and a second stimulation device for stimulation of the patient's contralateral ear via a fitting device communicatively connected to the first and second stimulation device for adjusting the first stimulation device and the second stimulation device;

the first stimulation device comprising an implantable neural stimulation arrangement comprising a plurality of stimulation channels for stimulating the ipsilateral ear at various stimulation sites according to a neural stimulation signal; and a sound processor for generating a neural stimulation signal for each stimulation channel from an input audio signal according to a neural stimulation model including a first set of stimulation parameters;

the second stimulation device comprising an audio signal processing unit for generating a stimulation signal from the input audio signal according to a stimulation model including a second set of stimulation parameters; and an output transducer for stimulation of the contralateral ear according to the stimulation signal;

the method comprising determining, for at least some of the stimulation channels, at least one of a hearing threshold neural stimulation signal level, a most comfortable neural stimulation signal level and an uncomfortable neural stimulation signal level;

calculating, by a data processing unit of the fitting device, for at least some audiometric frequencies at least one of an aided hearing threshold level, an aided most comfortable level and an aided uncomfortable level by taking into account the stimulation model of the second stimulation device and using the values of the second set of stimulation parameters as read from the second stimulation device, and calculating, by a data processing unit of the fitting device, for at least some audiometric frequencies, at least one of an aided hearing threshold level, an aided most comfortable level and an aided uncomfortable level from the stored hearing threshold neural stimulation signal level, most comfortable neural stimulation signal level and uncomfortable stimulation neural stimulation signal level by taking into account the stimulation model of the first stimulation device and using the values of the stimulation parameters as read from the first stimulation device;

presenting, to a user, by a graphical user interface of the fitting device, an acoustic level audiogram representation of at least one of the aided hearing threshold levels, the aided most comfortable levels and the aided uncomfortable levels as a function of the audiometric frequency both for neural stimulation by the first stimulation device and for stimulation by the second stimulation device.

* * * * *